United States Patent
Logan

(10) Patent No.: US 7,517,395 B2
(45) Date of Patent: Apr. 14, 2009

(54) SEAL HAVING LOW FRICTION NON-STICK SURFACE LAYER

(75) Inventor: Thomas M. Logan, Newtown Square, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 208 days.

(21) Appl. No.: 11/291,168

(22) Filed: Dec. 1, 2005

(65) Prior Publication Data

US 2007/0125234 A1 Jun. 7, 2007

(51) Int. Cl.
*B01D 53/02* (2006.01)
*F16J 15/10* (2006.01)

(52) U.S. Cl. .............. 96/105; 96/106; 95/89; 73/23.41; 277/652; 277/910; 277/945

(58) Field of Classification Search .......... 96/101, 96/104, 105, 106; 95/82, 85, 89; 73/23.35, 73/23.39, 23.41, 23.42; 277/626, 644, 645, 277/652, 654, 910, 918, 945
See application file for complete search history.

(56) References Cited

U.S. PATENT DOCUMENTS 2,859,061 A * 11/1958 Reid ................ 277/434
3,322,433 A * 5/1967 Rentschler ............ 277/652
3,549,156 A * 12/1970 Van Vleet et al. .......... 277/652
3,788,654 A * 1/1974 Mandley .............. 277/434
4,064,030 A * 12/1977 Nakai et al. ............ 204/192.36

(Continued)

OTHER PUBLICATIONS

"Surface Treatment Yields Low Friction Polymers," Feb. 1996, Sealing Technology, vol. 1996, Issue 26, p. 2.*

(Continued)

*Primary Examiner*—Duane S Smith
*Assistant Examiner*—Robert A Clemente
(74) *Attorney, Agent, or Firm*—Marc Bobys

(57) ABSTRACT

An inlet assembly for introducing a sample into a carrier gas stream for gas chromatography is disclosed including a housing having a bore that receives a liner. A sealing member having a core with a surface layer is positioned within the bore in sealing engagement with the bore and the liner. The surface layer of the sealing member has a lower adhesion to the housing than the core. The surface layer facilitates removal of the sealing member and the liner from the bore. A method of replacing an existing liner in an inlet assembly for chromatography is also disclosed. The method includes providing a liner with a sealing member having a core with a surface layer having a lower adhesion to the housing than the core, removing the existing liner from the bore and inserting a new liner with a new sealing member into the bore.

10 Claims, 1 Drawing Sheet

U.S. PATENT DOCUMENTS

| | | | | |
|---|---|---|---|---|
| 5,223,309 | A * | 6/1993 | Farivar et al. | 427/525 |
| 5,238,556 | A | 8/1993 | Shirkhan | |
| 5,328,557 | A * | 7/1994 | Blalock | 216/67 |
| 5,456,327 | A * | 10/1995 | Denton et al. | 175/371 |
| 5,551,706 | A * | 9/1996 | Barna et al. | 277/312 |
| 5,709,936 | A * | 1/1998 | Besmann et al. | 428/323 |
| 5,827,353 | A * | 10/1998 | O'Neil | 95/87 |
| 5,944,877 | A * | 8/1999 | O'Neil | 96/101 |
| 5,986,012 | A * | 11/1999 | Legare et al. | 525/326.2 |
| 6,488,992 | B1 * | 12/2002 | Boerio et al. | 427/447 |
| 6,540,264 | B1 * | 4/2003 | Yokoyama et al. | 285/319 |
| 6,623,545 | B2 * | 9/2003 | Thordarson et al. | 95/45 |
| 6,652,625 | B1 * | 11/2003 | Tipler et al. | 95/82 |
| 6,719,826 | B2 * | 4/2004 | Sasano et al. | 95/87 |
| 6,814,785 | B2 * | 11/2004 | Tipler et al. | 96/105 |
| 6,974,495 | B2 * | 12/2005 | Tipler et al. | 96/105 |
| 7,105,043 | B2 * | 9/2006 | O'Neil | 96/101 |

OTHER PUBLICATIONS

"Plasmapolymerisation Pretreatment and finishing of polymer surfaces In the field of medical plastics," Europlasma Technical Paper, pp. 1-7 (Sep. 2004).

"A new Alternative for Better Modification of Medical Surfaces and Textiles," Europlasma Technical Paper, (Aug. 2004).

"Plasma Technology: what is plasma?," (no other bibliographic information available).

* cited by examiner

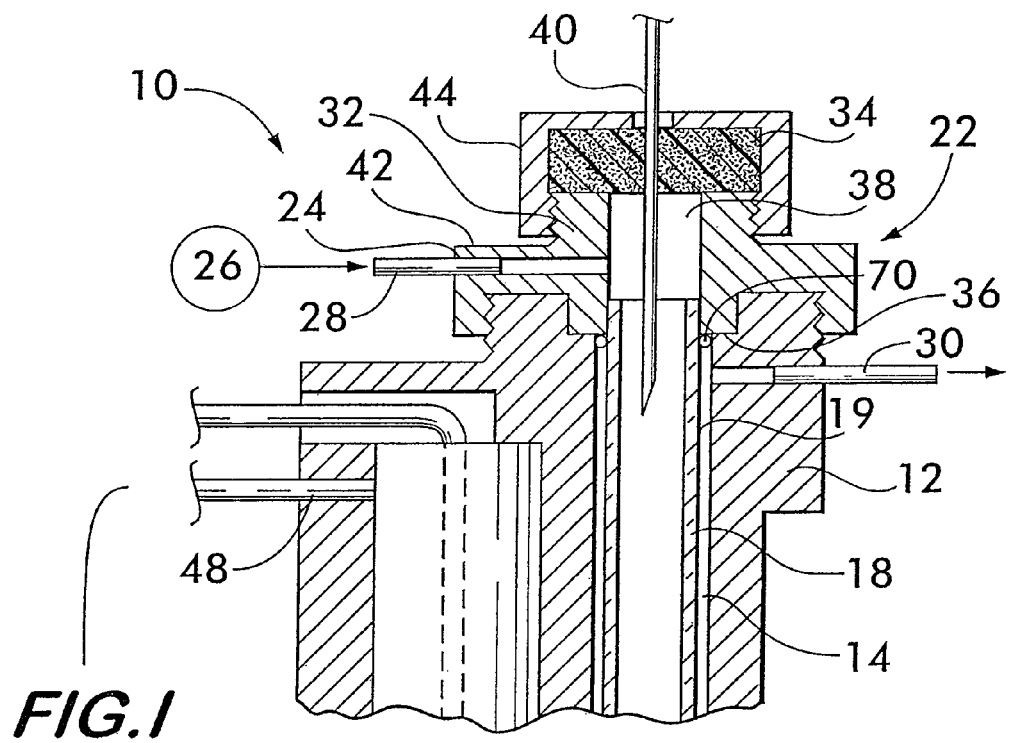
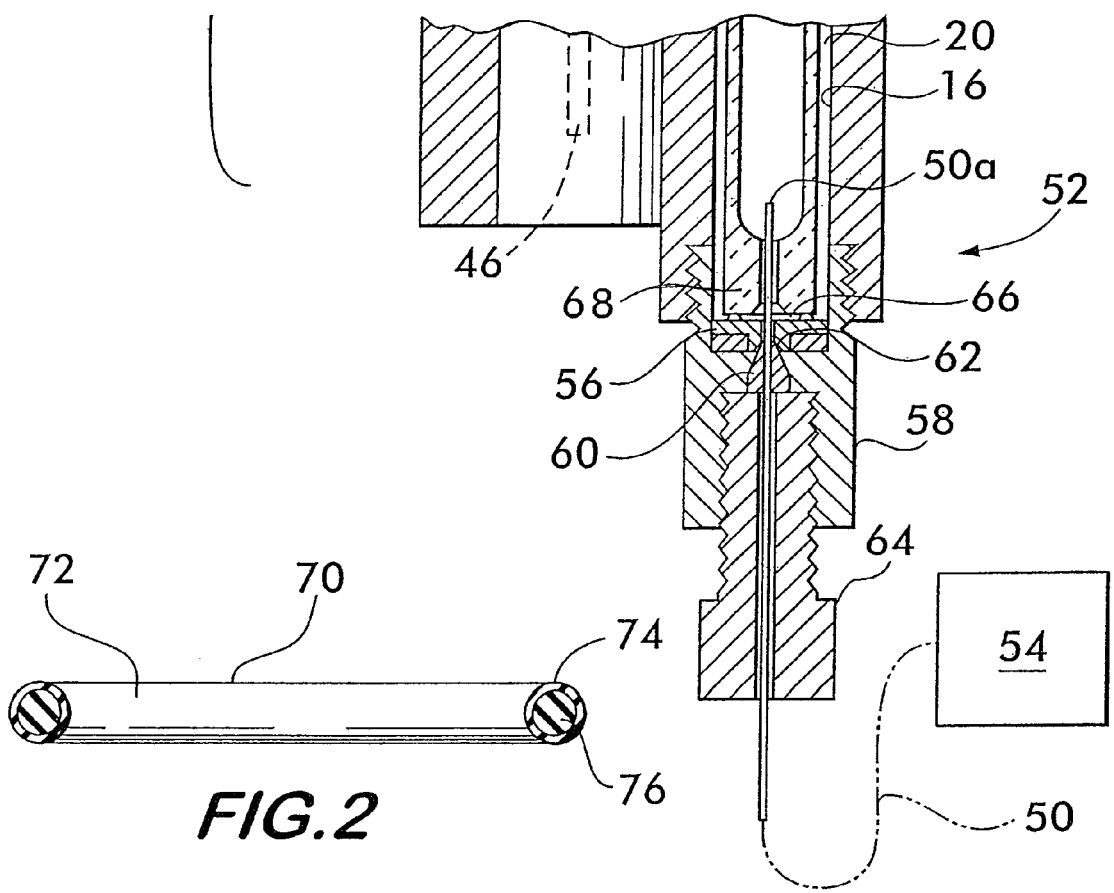

SEAL HAVING LOW FRICTION NON-STICK SURFACE LAYER

BACKGROUND

In one typical application of gas chromatography, a process by which one or more components from a chemical mixture may be separated and identified, a carrier gas, for example, an inert gas such as nitrogen or helium, flows through a tube known as a column. Large size columns may be packed with an inert packing medium coated with an active substance that interacts with components in the chemical mixture being analyzed. Smaller capillary columns are often coated on their inner surface with the active substance. A sample of the chemical mixture to be analyzed is introduced into the column. As the sample is swept through the column with the carrier gas, the different components, each one having a different affinity for the active substance lining the column or coating the packing medium, move through the column at different speeds. Those components having greater affinity for the active substance move more slowly through the column than those having less affinity, and this speed differential results in the components being separated from one another as they pass through and exit the column.

In the foregoing typical application, the carrier gas with the separated components exits the column and passes through a detector. Various types of detectors may be used, including a thermal conductivity detector, a flame ionization detector, electron capture detector, flame photometric detector, photoionization detector and a Hall electrolytic conductivity detector. A two dimensional plot of the detector measurements against elution time or volume, known as a chromatogram, may be made, and from the chromatogram or the digital representation thereof the components may be identified.

Introduction of the sample chemical mixture into the column may be effected using a sample inlet assembly. The inlet assembly has a bore in fluid communication with both a source of the carrier gas and the column. An injection port mounted on the inlet assembly is in fluid communication with the bore. The injection port receives a syringe for injecting the sample into the bore. Carrier gas flows from the source through the bore and into the column. The sample is injected into the bore where it is borne by the carrier gas into the column. The sample may initially be in a liquid state, and then vaporized to a gaseous state by the application of heat within the inlet assembly.

The bore has a removable liner made of glass or other substantially inert material to guard against contamination of the sample, which may react with the material comprising the inlet assembly. A seal, for example, an elastomeric O-ring, is positioned between the liner and the bore.

SUMMARY

The invention concerns a sealing member positionable between a liner and a bore of a chromatography inlet assembly. The sealing member comprises a core having a surface layer. The surface layer has a lower coefficient of friction than the core and facilitates removal of the sealing member from the bore.

The invention may also include an inlet assembly for introducing a sample into a carrier gas stream for gas chromatography. The inlet assembly is connectable to a chromatography column and includes a housing having a bore with an inner surface. A removable liner is positioned within the bore. The liner has an outer surface which may be in spaced relation to the inner surface of the bore. A sealing member is positioned within the bore in sealing engagement with the inner and outer surfaces. The sealing member has a core with a surface layer. The surface layer has a lower coefficient of friction than the core, which facilitates removal of the sealing member from the bore.

The invention also includes a method of replacing an existing liner in an inlet assembly for chromatography.

The method comprises:
  providing a liner having a sealing member comprising a core having a surface layer with a lower coefficient of friction than the core;
  removing the existing liner from the bore of the inlet assembly; and
  inserting the new liner with the sealing member into the bore.

BRIEF DESCRIPTION OF THE DRAWINGS

FIG. 1 is a longitudinal sectional view of a sample inlet assembly embodiment according to the invention; and FIG. 2 is a cross sectional view of a sealing member embodiment according to the invention.

DETAILED DESCRIPTION

FIG. 1 shows an embodiment of a sample inlet assembly 10 according to the invention and used for gas chromatography. Inlet assembly 10 comprises a housing 12, also known as an inlet assembly weldment. Housing 12 is often formed from stainless steel which provides a durable, robust design that mitigates contamination of samples being analyzed. Use of metal for the housing confers additional advantages as explained below.

A bore 14 having an inner surface 16 extends through housing 12. A liner 18 is positioned within the bore. The liner is often formed from an inert material, for example, glass or fused quartz, and helps to mitigate contamination of the gas sample and carrier gas passing through the bore. Liner 18 has a diameter that is smaller than the diameter of the bore, and together the outer surface 19 of the liner and the inner surface 16 of the bore define an annular duct 20 that extends along bore 14. Duct 20 provides a fluid flow path for gas that does not pass through the column, and thus enables the flow to be split as described in detail below.

The upstream end 22 of housing 12 has a carrier gas inlet 24 that is in fluid communication with a source of carrier gas 26 through a conduit 28. Carrier gas inlet is in fluid communication with bore 14 through the liner 18. A gas outlet 30 is also positioned on the housing 12, the outlet 30 being in fluid communication with the annular duct 20 between the bore and the liner.

The upstream end 22 of housing 12 also has a sample inlet 32 in fluid communication with bore 14 through the liner 18. Sample inlet 32 includes a septum 34 that is exposed to the ambient. Septum 34 overlies an inlet seat 36 that interfaces with the liner 18. An aperture 38 extends through the inlet seat to permit a syringe needle 40 to be inserted into the liner 18 and introduce the sample into the sample inlet assembly 10. The syringe needle penetrates the septum 34 before it passes through aperture 38. The septum is a solid body formed of a soft polymer material. The material permits the needle to pass through but "heals" itself by closing any opening formed by the needle, thereby allowing the septum to act as a seal for the inlet seat 36 that prevents gases from exiting to the ambient through aperture 38. Both the inlet seat 36 and the septum 34 are secured to the housing 12 by respective retaining nuts 42 and 44, allowing for removal of the seat and the septum as well as the liner 18.

A heating element 46 and a thermistor 48 are mounted on the housing 12. The heater is electrically powered and heats the housing to the temperature required to vaporize any liquid sample to the gaseous state. The thermistor measures the housing temperature and provides feedback information to help maintain the housing at a desired temperature appropriate to the sample being analyzed.

A chromatography column 50 is connected to the downstream end 52 of the inlet assembly 10. Large columns may have inner diameters between about 3 mm and about 8 mm and lengths between about 1 meter and about 3 meters. Capillary columns (as shown) may have inner diameters between about 0.05 mm and about 1 mm and may be 100 meters or more in length. Column 50 is in fluid communication with the bore 14 through the liner 18 and conducts the carrier gas and sample passing through the bore to a chromatograph 54, indicated schematically. Fluid communication between the column 50 and the bore 14 is effected by a sealing plate 56 that engages the downstream end of the inlet assembly to seal the bore 14. Sealing plate 56 is held in position by a retaining nut 58. The column 50 has a ferrule 60 that engages a seat 62 on the sealing plate 56. The ferrule 60 is kept engaged with the seat 62 by a retaining nut 64.

To enable split flow of the gases through the inlet assembly there is a gas space 66 between the end 68 of liner 18 and the sealing plate 56. Gas space 66 provides fluid communication between the liner 18 and the annular duct 20. This allows a portion of the gases to bypass the intake 50a of column 50, exit the liner 18 into the gas space 66 and then travel along the annular duct 20 to exit the inlet assembly 10 through the gas outlet 30. The proportion of the gas that passes through the column may be controlled by throttling the gas outlet 30.

A sealing member 70 is positioned within bore 14. Sealing member 70 isolates the interior of the liner 18 from the bore 14 to ensure that the gas flow proceeds downstream through the liner to the column 50, and, for the portion of the gas not entering the column, upstream through annular duct 20 to the gas outlet 30.

Sealing member 70 is an O-ring in sealing engagement with the outer surface 19 of liner 18 and the inner surface 16 of bore 14. A typical O-ring seal used with a chromatography inlet assembly is shown in FIG. 2 and has a torroidal shape and may have an inner diameter of about 0.239 inches defining a central space 72 for receiving the liner. The thickness of the O-ring is about 0.070 inches. A durometer of about 75 on the Shore A scale has shown itself to be practical for such seals.

Sealing member 70 is formed from a fluorocarbon rubber compound, that is, a fluorocarbon polymer which exhibits sufficient elasticity to allow it to act as a seal in the gas chromatograph environment as described herein. An example of such a fluorocarbon rubber compound is supplied by DuPont under the trade name Viton. Viton is used with analysis samples formed of chemically aggressive compounds such as chlorinated solvents, benzene, toluene, alcohols, hexane and heptane because it is substantially impervious to chemical attack by such compounds. Viton is also useful in view of its ability to form an effective seal even at the elevated temperatures (300 degrees C. or greater) required to volatilize the-sample components for gas chromatography.

Over time, after many cycles of heating and cooling of the inlet assembly, the fluorocarbon rubber seal 70 may adhere to the inner surface 16 of bore 14. This makes it difficult to remove the liner 18, for example, to replace an old, contaminated liner with a new one. Adhesion between the sealing member and the bore may also cause particles of fluorocarbon rubber to be left on the inner surface of the bore, and these particles can contaminate the gases flowing through the inlet assembly and may adversely affect column performance.

To avoid these problems the sealing member 70 is treated so that, as shown in FIG. 2, it has a polymerized surface layer 74 surrounding a core 76. The surface layer 74 exhibits lower adhesion to the housing than the untreated core 76. One way of evaluating the adhesion of the sealing member to the housing is to measure the coefficient of friction of the surface layer in comparison with that of the core. The treated surface layer has a lower coefficient of friction than the untreated material forming the core and therefore exhibits the desired non-stick characteristics. The non-stick characteristic of the surface layer prevents the seal from adhering to the inner surface 16 of bore 14 and thus facilitates removal and replacement of liners 18 in addition to mitigating contamination of the inlet assembly by leaving particles of the sealing member behind upon removal of the liner.

Because the surface layer 74 is very thin (on the order of microns in thickness) the sealing member substantially retains the desired physical characteristics, such as resistance to chemical attack and relatively high melting point associated with the core material, but also will not stick to the housing 12.

Surface layer 74 is formed by plasma treatment of the sealing member 70. Plasma treatment is effected by electrically energizing a process gas at low pressures (1-100 Pa) within a vacuum chamber in which the sealing member 70 is positioned. The atoms or molecules forming the process gas are ionized, and the molecules may be fragmented, and thus the process gas becomes highly reactive and will readily react chemically with the exposed surfaces of the sealing member.

Specific surface properties on the sealing member may be obtained through the choice of the process gas as explained in the technical papers *Plasmapolymerization Preteratment and Finishing of Polymer Surfaces in the Field of Medical Plastics*, Sep. 9, 2004, Europlasma, Oudenaarde, Belgium, and *A New Alternative for Better Modification of Medical Surfaces and Textiles*, Aug. 5, 2004, Europlasma, Oudenaarde, Belgium, both articles being hereby incorporated by reference. Reduction of the surface friction coefficient to ensure the desired non-stick characteristics is obtained by gases which effect a surface deposition or polymerization layer on the sealing member. The molecular structure in the surface layer 74 is highly cross-linked and built up from the ions and fragments of the process gas, formed into a plasma by the energy of the electrical discharge within the vacuum chamber. Plasma polymerization, as opposed to other plasma processes (such as surface activation, modification, etching, and degreasing) uses process gases, both alone and in combination, including hydrocarbons such as acetylene, ethane, ethylene, and methane, chemical analogues of these gases for example formed by substituting suitable elements for the carbon atoms as are known to those of skill in the art. Other analogues include fluorocarbon gases such as $C_2F_4$, $C_2F_6$ and the like, again used either alone or in combination with one another or with the hydrocarbons mentioned above. Interaction between the process gas plasma fragments and the surface of the sealing member produces chemically stable structures in the surface layer 74 while removing unstable chemical structures by the reaction with chemically active fragments to form the desired surface characteristics. Chromatography Research Supplies, Inc. of Louisville, Ky. have provided plasma treated Viton O-ring seals which have been used with sample inlet assemblies as described above with the desired results.

What is claimed is:

1. An inlet assembly for introducing a sample into a carrier gas stream for gas chromatography, said inlet assembly being connectable to a chromatograph column, said inlet assembly comprising:
    a housing having a bore with an inner surface;
    a removable liner positioned within said bore, said liner having an outer surface in spaced relation to said inner surface of said bore;
    a sealing member positioned within said bore in sealing engagement with said inner and outer surfaces, said sealing member having a core of untreated material surrounded by a thin surface layer of said material treated so as to chemically alter said material such that said treated material of said thin surface layer has a lower coefficient of friction than said untreated material of said core, said treated material of said thin surface layer thereby facilitating removal of said sealing member from said bore, wherein the thickness of the thin surface layer relative to the diameter of the core of untreated material is selected so that the sealing member provides a means for preventing the sealing member from sticking to the inner surface of the bore;
    a carrier gas inlet in fluid communication with said bore;
    an injection port in fluid communication with said bore; and
    a fitting adapted for connecting said chromatograph column in fluid communication with said bore.

2. An inlet assembly according to claim 1, wherein said sealing member comprises an O-ring.

3. An inlet assembly according to claim 1, wherein said housing is formed from stainless steel.

4. An inlet assembly according to claim 1, wherein said liner is formed of glass.

5. An inlet assembly according to claim 1, wherein said core and said surface layer are formed from a fluoroelastomer.

6. An inlet assembly according to claim 5, wherein said material comprising said surface layer is polymerized using a process gas comprising a hydrocarbon or chemical analogs thereof.

7. An inlet assembly according to claim 5, wherein said material comprising said surface layer is polymerized using a process gas comprising acetylene, ethane, ethylene, methane or chemical analogues thereof 8. A method of replacing an existing liner in an inlet assembly for chromatography comprising a housing having a bore with an inner surface, said method comprising:
    providing a liner having an outer surface;
    providing a sealing member comprising a core of untreated material surrounded by a thin surface layer of said material treated so as to chemically alter said material such that said treated material of said thin surface layer has a lower coefficient of friction than said untreated material of said core;
    positioning the liner therein the bore;
    positioning the sealing member therebetween the outer surface of the liner and the inner surface of the bore, wherein the thickness of the thin surface layer relative to the diameter of the core of untreated material is selected so that the sealing member provides a means for preventing the sealing member from sticking to the inner surface of the bore;
    removing said existing liner from a bore of said inlet assembly; and
    inserting said new liner with said sealing member into said bore.

9. A method according to claim 8, further comprising providing a sealing member formed of a fluorocarbon rubber compound.

10. A method according to claim 8, wherein said sealing member is provided having a polymerized surface layer formed by a plasma treatment.

* * * * *